United States Patent [19]

Yamamoto et al.

[11] 4,246,178
[45] Jan. 20, 1981

[54] TETRAHYDROPYRAN-5-ONE COMPOUNDS

[75] Inventors: Akira Yamamoto; Kenichi Taguchi; Akira Hayashida, all of Joetsu; Toshinobu Ishihara, Niigata, all of Japan

[73] Assignee: Shin-Etsu Chemical Co., Ltd., Japan

[21] Appl. No.: 952,457

[22] Filed: Oct. 18, 1978

[30] Foreign Application Priority Data

Dec. 12, 1977 [JP] Japan ................................ 52-149605

[51] Int. Cl.$^3$ ............................................. C07D 309/06
[52] U.S. Cl. ........................ 260/345.8 R; 260/345.9 R
[58] Field of Search .................. 260/345.9 R, 345.8 R

[56] References Cited

U.S. PATENT DOCUMENTS

| | | | |
|---|---|---|---|
| 4,059,595 | 11/1977 | Shono et al. | 260/345.9 R |
| 4,082,717 | 4/1978 | Brennan et al. | 260/345.9 R |
| 4,126,624 | 11/1978 | Brennan et al. | 260/345.9 R |
| 4,150,039 | 4/1979 | Harima et al. | 260/345.9 R |

OTHER PUBLICATIONS

Shono et al., Tetrahedron Letters, No. 17, 1363 (1976).
Torii et al., Chemistry Letters, vol. 5, 495 (1976).

*Primary Examiner*—Nicky Chan
*Attorney, Agent, or Firm*—McGlew and Tuttle

[57] ABSTRACT

A novel class of tetrahydropyran-5-one compounds are provided which are 2-alkoxy- or 2-acyloxy-3,4-dihalogeno-6-alkyl tetrahydropyran-5-ones expressed by the general formula

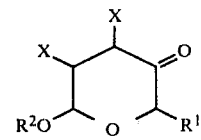

where $R^1$ is an alkyl group, $R^2$ is an alkyl or an acyloxy group and X is a halogen atom. The compounds are synthesized by the reaction of a 2-furyl carbinol compound with a halogen in the presence of an alcohol or a carboxylic acid. The compounds are useful as an intermediate for the synthetic preparation of various useful compounds including maltol as a flavor.

4 Claims, 2 Drawing Figures

TETRAHYDROPYRAN-5-ONE COMPOUNDS

BACKGROUND OF THE INVENTION

The present invention relates to a novel tetrahydropyran-5-one compound useful as an intermediate for the synthesis of various organic compounds, e.g. those used as a flavor. In particular, the present invention relates to a 2-hydrocarbyloxy- or 2-acyloxy-3,4-dihalogeno-6-hydrocarbyl-tetrahydropyran-5-one compound.

2-Alkyl-3-hydroxy-4H-pyran-4-one compounds, e.g. 2-methyl-3-hydroxy-4-pyrone, which is called maltol, are important organic compounds useful as a flavoring material in foods and stock feeds with increasing demand in recent years. No convenient synthetic methods have been known for the preparation of maltol. Conventionally, according to a fermentative method, kojic acid obtained by fermentation is converted into the objective compound through four steps including oxidation and decarboxylation. This process is disadvantageous due to the lengthy sequence of the steps taking about one week for the fermentation as well as due to the necessity of large-scaled facility for the fermentation step, precious metal catalyst in the oxidation step and a high temperature of 250° C. or higher in the decarboxylation step.

On the other hand, a synthetic method for the preparation of maltol is disclosed in Japanese Patent Disclosure No. 52-31077 starting with a 2-furyl carbinol compound. The method comprises the steps of an electrolysis or reaction of the 2-furyl carbinol compound with a halogen as dissolved in an alcohol to introduce alkoxy groups to the 2- and 5-positions of the furan ring, reaction of a strong organic acid with the 2, 5-dialkoxy furyl derivative above obtained to the formation of a 5,6-dihydro-2H-pyran-5-one derivative, epoxidization of the above compound at the 3- and 4-positions, and finally a rearrangement reaction of the epoxy compound to the objective compound.

The above-described synthetic method is also disadvantageous due to the length of the reaction steps as well as due to the danger of explosion resulting from the use of a peroxide, such as hydrogen peroxide, in the epoxidization step. Such danger may be avoided only by carrying out the reaction at a relatively low temperature at the sacrifice of reaction velocity.

The compounds of the present invention have been discovered as an intermediate compound in the course of extensive investigations undertaken by the inventors to establish a novel and advantageous route for the synthetic preparation of 2-alkyl-3-hydroxy-4H-pyran-4-one compounds including maltol.

SUMMARY OF THE INVENTION

The novel compounds disclosed in the present invention are 2-hydrocarbyloxy- or 2-acyloxy-3,4-dihalogeno-6-hydrocarbyl-tetrahydropyran-5-one compounds represented by the general formula

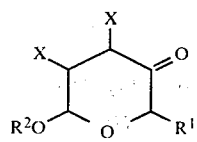   (I)

where $R^1$ is a hydrogen atom or a monovalent hydrocarbon group having 1 to 7 or, particularly, 1 or 2 carbon atoms, $R^2$ is a monovalent hydrocarbon group or an acyl group having 1 to 7 carbon atoms and X is a halogen atom.

The compounds, which are novel compounds not described hitherto in literature, are prepared by the reaction of a 2-furyl carbinol compound represented by the general formula

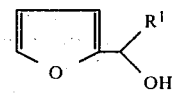   (II)

where $R^1$ has the same meaning as defined above, with a halogen in the presence of an alkali and an alcohol or a carboxylic acid represented by the general formula $R^2OH$ where $R^2$ has the same meaning as defined above.

The dihalogeno derivatives of the present invention are readily hydrolyzed into 3-hydroxy-4-pyrone compounds, e.g. maltol, as the final product having a wide range of applications.

DETAILED DESCRIPTION OF THE PREFERRED EMBODIMENTS

Figure 1:
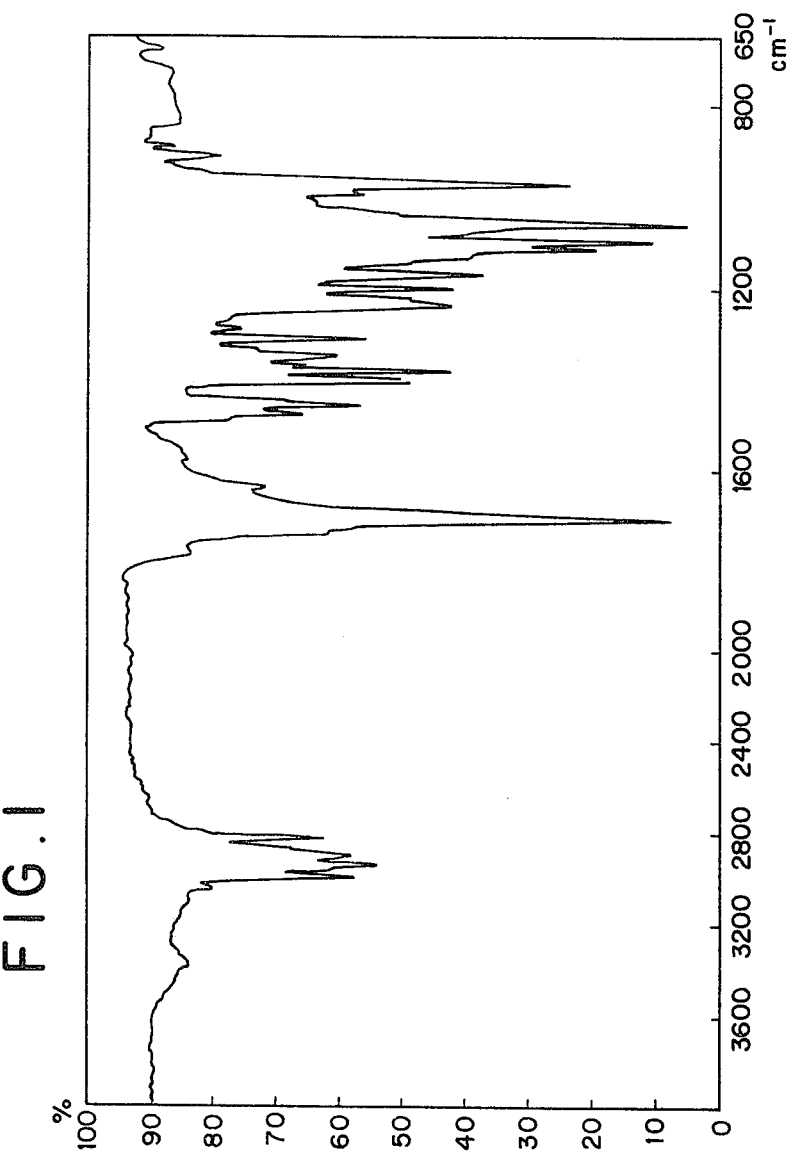
FIG. 1 shows the infrared absorption spectrum of 5,6-dihydro-2-methoxy-6-methyl-2H-pyran-5-one used as a comparative material in Example 1.

In the method for the preparation of the objective 3,4-dihalogeno derivatives, a 2-furyl carbinol compound represented by the general formula (II) above is used as the starting material. In the general formula (II), the group represented by the symbol $R^1$ is a hydrogen atom or a monovalent hydrocarbon group having 1 to 7 carbon atoms exemplified by alkyl groups, such as methyl, ethyl, propyl, butyl and hexyl groups; alkenyl groups, such as vinyl and allyl groups; and aromatic groups, such as phenyl and benzyl groups. The examples of the 2-furyl carbinol compounds other than furfuryl alcohol, where the group $R^1$ is a hydrogen atom, are 2-furylmethyl carbinol, 2-furylethyl carbinol, 2-furylpropyl carbinol, 2-furylhexyl carbinol, 2-furylvinyl carbinol, 2-furylphenyl carbinol, 2-furylbenzyl carbinol and the like. These furyl carbinol compounds are commercially available.

The furyl carbinol compound is brought into reaction with a halogen, e.g. chlorine or bromine, and an alcohol or a carboxylic acid represented by the general formula $R^2OH$ where $R^2$ is a monovalent hydrocarbon group or an acyl group having 1 to 7 carbon atoms. The alcohols are exemplified by methyl alcohol, ethyl alcohol, n-propyl alcohol, isopropyl alcohol, n-butyl alcohol, isobutyl alcohol, hexyl alcohol, allyl alcohol, crotyl alcohol, phenol, benzyl alcohol and the like. The carboxylic acids are exemplified by acetic acid, propionic acid and the like. The reaction is carried out with two moles of the halogen per mole of the furyl carbinol compound, preferably, in the presence of an alkali.

The reaction is carried out in a manner such that the halogen is introduced into a reaction vessel containing the furyl carbinol compound and the alcohol or carboxylic acid, optionally, together with an organic solvent kept at a temperature in the range from −50° to +100°

C. or, preferably, from −30° to +50° C. under agitation. The reaction is an exothermic reaction, so that it is usually necessary to cool the reaction vessel from outside in order to avoid the excessive elevation of temperature.

The alcohol or carboxylic acid represented by the general formula $R^2OH$ is used in an amount of at least 3 moles or, preferably, from 8 to 15 moles per mole of the furyl carbinol compound. The stoichiometric amount of the halogen to be reacted with one mole of the furyl carbinol compound is 2 moles. However, a small excess of the halogen over 2 moles may be used in some cases per mole of the furyl carbinol compound in order to complete the reaction as rapidly as possible, since the reaction velocity with the second one mole portion of the halogen is somewhat smaller than with the first one mole portion of the halogen. It is recommendable that the reaction mixture is subjected to continued agitation for a while after completion of the introduction of the halogen, while maintaining the above-mentioned reaction temperature.

In the above-described method for the synthesis of the objective dihalogeno derivatives, the yield of the product can be further increased by the presence of an alkaline substance in the reaction mixture. The alkaline substance suitable for the purpose is exemplified by metals of alkali, such as sodium and potassium and hydroxides, oxides, alcoholates and organic acid salts of alkali metals and alkaline earth metals, such as sodium hydroxide, potassium hydroxide, calcium oxide, sodium methoxide, sodium ethoxide, sodium acetate, calcium oxalate, sodium carbonate, potassium carbonate, sodium hydrogen-carbonate and the like.

While the addition of an alkaline substance into the reaction mixture is advantageous to increase the yield of the objective product, an excessive amount of the alkaline substance has an adverse effect of decreasing the reaction velocity. Accordingly, the amount of the alkaline substance should not exceed 3 moles per mole of the furyl carbinol compound or, preferably, in the range from 1.6 to 2.1 moles per mole of the furyl carbinol compound.

Furthermore, the reaction with the halogen must be carried out in a state as dry as possible or in the substantial absence of water, since the presence of a small amount of water in the reaction mixture remarkably reduces the yield of the objective product, although such an amount of water as produced by the neutralization of the alkaline substance may be permissible.

It is optional that, if necessary, the reaction mixture in the reaction with the halogen is diluted with an organic solvent as a reaction medium, or the use of an organic solvent is rather recommendable, especially when the alcohol or carboxylic acid represented by the general formula $R^2OH$ is solid at the temperature of the reaction. Suitable solvents for such a purpose are those which are inert to the action of the halogen at the temperature of the reaction, such as methylene chloride, carbon tetrachloride, dichloroethane, diethyl ether, benzene, toluene, dioxane and the like.

The thus-obtained reaction mixture after completion of the reaction with the halogen is subjected to the removal of the precipitated salt and then to distillation to remove the solvent and the excess of the halogen when an excess amount of the halogen has been used to give the objective 3,4-dihalogeno derivative expressed by the formula (I) in a high yield.

It is an advantageous process that the reaction mixture after completion of the reaction with the halogen is subjected as such to the hydrolysis at an elevated temperature before the removal of the salt and the solvent to be converted into the 3-hydroxy-4-pyrone compound without any adverse effects on the yield of the final objective compound.

As has been described above, the necessary steps in the reaction of the method of the present invention are only the introduction of the halogen and, in some cases, aging for certain duration so that the objective dihalogeno derivative can be obtained conveniently and economically within a short time. Thus, the present invention is very valuable in presenting an advantageous means for the synthetic preparation of the 3-hydroxy-4-pyrone compounds including maltol.

The following examples illustrate the present invention in further detail but not to limit the scope of the invention.

EXAMPLE 1

Into a reaction vessel were taken 75 ml of methyl alcohol and 5.75 g (0.25 mole) of sodium metal to form a homogeneous solution. To this solution, 14 g (0.125 mole) of 2-furylmethyl carbinol was added, followed by introduction of 17.75 g (0.25 mole) of chlorine over a period of 20 minutes with cooling with ice from outside to keep the reaction mixture at a temperature of 20° to 30° C. under agitation. The agitation was continued further for 30 minutes after the end of the introduction of the chlorine.

The reaction mixture thus obtained was filtered to remove the by-product sodium chloride and, after removal of the solvent by distillation, admixed with dry ether, followed by a second distillation to remove a trace amount of sodium chloride. Stripping of the resultant mixture to remove the solvent and other low boiling matters by distillation under reduced pressure at a temperature not exceding 20° C. gave 21.0 g of a reaction product.

The thus-obtained compound was identified to be 2-methoxy-3,4-dichloro-6-methyl tetrahydropyran-5-one having the following structural formula

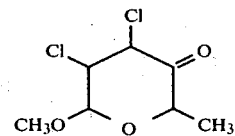

from the results of elementary analysis, infrared absorption spectral analysis, nuclear magnetic resonance absorption spectral analysis and mass spectrometric analysis. Details of the analyses were as follows.

Elementary analysis: Found: C, 39.58%; H, 4.71%; and Cl, 33.02%. Calculated: C, 39.46%; H, 4.73%; and Cl, 33.28%.

The calculated values were for $C_7H_{10}O_3Cl_2$ which corresponded to 2-methoxy-3,4-dichloro-6-methyl tetrahydropyran-5-one.

Infrared absorption spectral analysis

Figure 2:
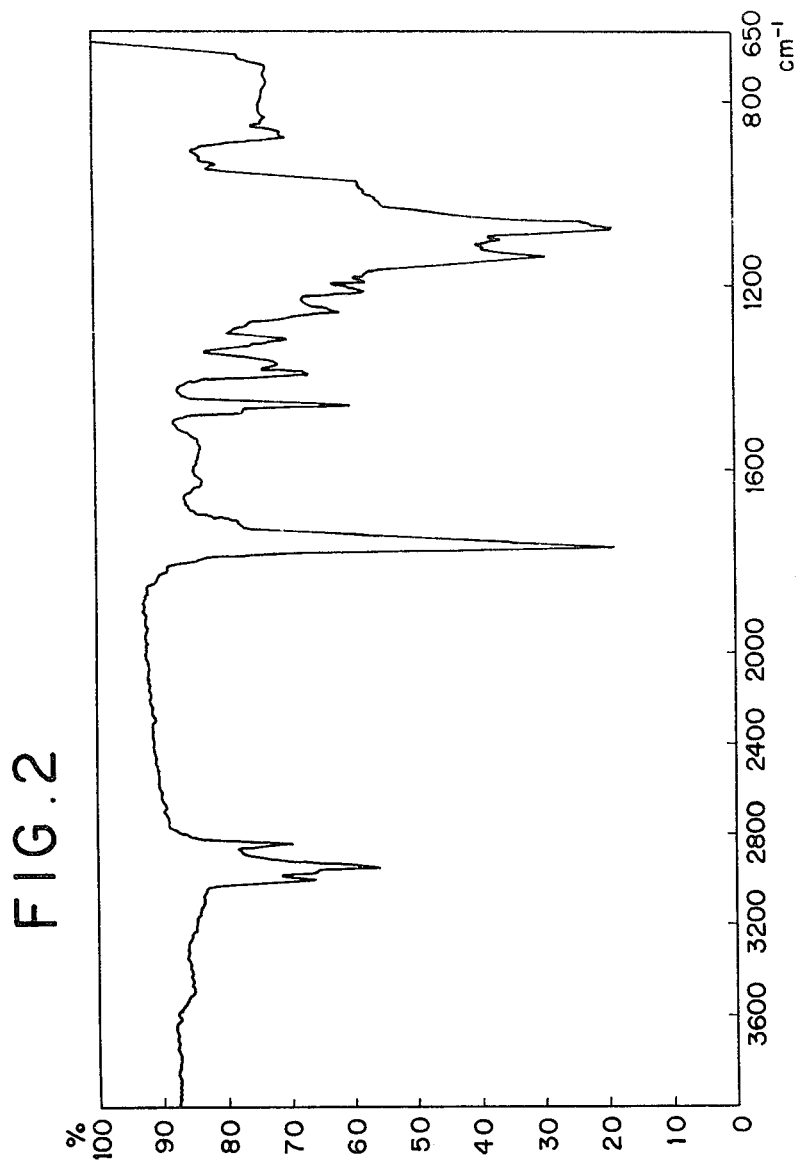
FIG. 2 shows the infrared absorption spectrum of the reaction product obtained in Example 1.

The infrared absorption spectra of 5,6-dihydro-2-methoxy-6-methyl-2H-pyran-5-one as a comparative material and the reaction product are shown in FIG. 1 and FIG. 2, respectively. The absorption bands appearing in FIG. 1 at 2840, 1710, 1640 and 1060 cm$^{-1}$ are assigned to OCH₃, C=O, C=C and C—O—C groups, respectively, while the spectrum shown in FIG. 2 has absorption bands at 2840, 1760 and 1060 cm⁻¹ to be assigned to OCH₃, C=O and C—O—C groups, respectively, but no absorption band near 1640 cm⁻¹ indicating the disappearance of the =C=C= linkages. The shift of the C=O absorption band toward higher wave number indicates the presence of a chlorine atom at the α-position.

NMR absorption spectrum

The assignment of the absorption in 5,6-dihydro-2-methoxy-6-methyl-2H-pyran-5-one as the comparative material was as follows. Two positions in the absorption were obtained due to the presence of the stereoisomers.

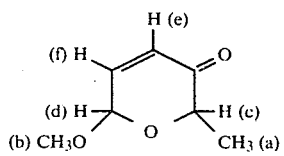

| | (δ) ppm | |
|---|---|---|
| (a) | 1.34 | 1.43 |
| (b) | 3.45 | |
| (c) | 4.41 | 4.10 |
| (d) | 4.97 | 5.13 |
| (e) | 5.96 | 5.98 |
| (f) | 6.74 | 6.76 |

Except that the absorption corresponding to the H atom in the 3- and 4-positions in the above comparative material appeared as shifted toward higher magnetic field due to the addition of the chlorine atoms, the results in the reaction product were much the same as in the above.

Mass spectrometric analysis

The parent peaks of (M-1) appearing at 211, 213 and 215 had intensity ratios of approximately 9:6:1 corresponding to the isotopic abundance ratio of about 3:1 of the chlorine isotopes with mass numbers of 35 and 37 indicating that the compound had two chlorine atoms in a molecule.

EXAMPLE 2

The same experimental procedure as in Example 1 was repeated except that methyl alcohol was replaced with the same volume of ethyl alcohol to give 21.5 g of a reaction product. The analytical results of this reaction product were as follows.

Elementary analysis: Found: C, 42.53%; H, 5.25%; and Cl, 31.01%. Calculated: C, 42.31%; H, 5.33%; and Cl, 31.22%.

The calculated values were for C₈H₁₂O₃Cl₂.

Infrared absorption spectral analysis

Strong absorption bands were found at 1760 and 1060 cm⁻¹ assigned to C=O and C—O—C linkages, respectively.

Mass spectrometric analysis

The parent peaks of (M-1) appeared at 225, 227 and 229 with the intensity ratios of approximately 9:6:1 leading to the same conclusion as given in Example 1.

The above analytical results supported that the product compound was 2-ethoxy-3,4-dichloro-6-methyl tetrahydropyran-5-one having the following structural formula.

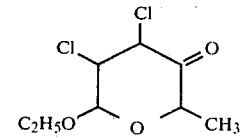

EXAMPLE 3

The same experimental procedure as in Example 1 was repeated except that methyl alcohol was replaced with the same volume of acetic acid to give 24 g of a reaction product. The analytical results of this compound were as follows. As a result, the compound was found to be 2-acetoxy-3,4-dichloro-6-methyl tetrahydropyran-5-one having the following structural formula.

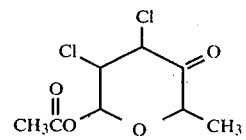

Elementary analysis: Found: C, 39.97%; H, 4.16%; and Cl, 29.18%. Calculated: C, 39.86%; H, 4.18%; and Cl, 29.41%.

The calculated values were for C₈H₁₀O₄Cl₂.

Infrared absorption spectral analysis

The characteristic absorption bands in the spectrum appeared at 1760, 1750 and 1240 cm⁻¹ assigned to ketone-type C=O linkages, ester-type C=O linkages and C—O—C linkages, respectively.

Mass spectrometric analysis

The parent peaks of (M-1) appeared at 239, 241 and 243 with the intensity ratios of approximately 9:6:1 leading to the same conclusion as given in Example 1.

The above described analytical results as well as the comparison of the infrared absorption spectrum with the spectrum of a related compound given below supported that the reaction product was 2-acetoxy-3,4-dichloro-6-methyl tetrahydropyran-5-one.

For comparative purposes, a known related compound 2-acetoxy-6-methyl-5,6-dihydropyran-5-one having the structural formula

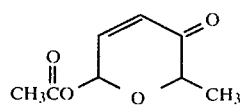

was analyzed by infrared absorption spectrometry giving the absorption bands at 1750, 1710, 1640 and 1240 cm⁻¹ assigned to ester-type C=O linkages, ketone-type

EXAMPLE 4

The same experimental procedure as in Example 1 was repeated except that 2-furylmethyl carbinol was replaced with 15.75 g (0.125 mole) of 2-furylethyl carbinol, to give 22.5 g of a reaction product which was identified by the under-mentioned analytical results to be 2-methoxy-3,4-dichloro-6-ethyl tetrahydropyran-5-one having the following structural formula

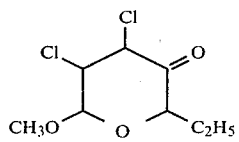

Elementary analysis: Found: C, 42.59%; H, 5.40%; and Cl, 31.01%. Calculated: C, 42.31%; H, 5.33%; and Cl, 31.22%.

The calculated values were for $C_8H_{12}O_3Cl_2$.

Infrared absorption spectral analysis

The characteristic absorption bands appeared in the spectrum at 2840, 1760 and 1060 cm$^{-1}$ assigned to $OCH_3$, $C=O$ and $C-O-C$ linkages, respectively.

Mass spectrometric analysis

The parent peaks of (M-1) appeared at 225, 227 and 229 with the intensity ratios of approximately 9:6:1 leading to the same conclusion as given in Example 1.

The above described analytical results as well as the comparison of the infrared absorption spectrum with the spectrum of a related compound given below supported that the reaction product was 2-methoxy-3,4-dichloro-6-ethyl tetrahydropyran-5-one.

For comparative purposes, a known related compound 2-methoxy-6-ethyl-5,6-dihydropyran-5-one having the structural formula

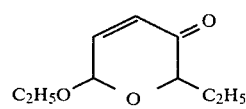

was analyzed by infrared absorption spectrometry giving the absorption bands at 2840, 1710, 1640 and 1060 cm$^{-1}$ assigned to $OCH_3$, $C=O$, $C=C$ and $C-O-C$ linkages, respectively.

EXAMPLE 5

The same experimental procedure as in Example 2 was repeated except that 2-furylmethyl carbinol was replaced with 15.75 g of 2-furylethyl carbinol, to give 23 g of a reaction product which was identified by the under-mentioned analytical results to be 2-ethoxy-3,4-dichloro-6-ethyl tetrahydropyran-5-one having the following structural formula.

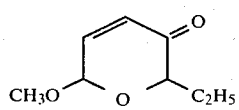

Elementary analysis: Found: C, 44.82%; H, 5.82%; and Cl, 29.20%: Calculated: C, 44.83%; H, 5.85%; and Cl, 29.41%.

The calculated values were for $C_9H_{14}O_3Cl_2$.

Infrared absorption spectral analysis

The characteristic absorption bands appeared in the spectrum at 1760 and 1060 cm$^{-1}$ assigned to $C=O$ and $C-O-C$ linkages, respectively.

Mass spectrometric analysis

The parent peaks of (M-1) appeared at 239, 241 and 243 with the intensity ratios of approximately 9:6:1 leading to the same conclusion as given in Example 1.

The above described analytical results as well as the comparison of the infrared absorption spectrum with the spectrum of a related compound given below supported that the reaction product was 2-ethoxy-3,4-dichloro-6-ethyl tetrahydropyran-5-one.

For comparative purposes, a known related compound 2-ethoxy-6-ethyl-5,6-dihydropyran-5-one having the structural formula

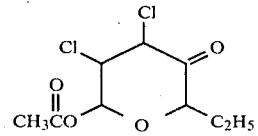

was analyzed by infrared absorption spectrometry giving the absorption bands at 1710, 1640 and 1060 cm$^{-1}$ assigned to $C=O$, $C=C$ and $C-O-C$ linkages, respectively.

EXAMPLE 6

The same experimental procedure as in Example 3 was repeated except that 2-furylmethyl carbinol was replaced with 15.75 g of 2-furylethyl carbinol, to give a 25 g reaction product which was identified by the under-mentional analytical results to be 2-acetoxy-3,4-dichloro-6-ethyl tetrahydropyran-5-one having the following structural formula.

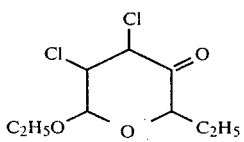

Elementary analysis Found: C, 42.41%; H, 4.70%; and Cl, 27.21%. Calculated: C, 42.37%; H, 4.74%; and Cl, 27.80%.

The calculated values were for $C_9H_{12}O_4Cl_2$.

Infrared absorption spectral analysis

The characteristic absorption bands appeared in the spectrum at 1760, 1750 and 1240 cm$^{-1}$ assigned to ketone-type $C=O$, ester-type $C=O$ and $C-O-C$ linkages, respectively.

Mass spectrometric analysis

The parent peaks of (M-1) appeared at 253, 255 and 257 with the intensity ratios of approximately 9:6:1 leading to the same conclusion as given in Example 1.

The above described analytical results as well as the comparison of the infrared absorption spectrum with the spectrum of a related compound given below supported that the reaction product was 2-acetoxy-3,4-dichloro-6-ethyl tetrahydropyran-5-one.

For comparative purposes, a known related compound 2-acetoxy-6-ethyl-5,6-dihydropyran-5-one having the structural formula

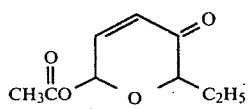

was analyzed by infrared absorption spectral analysis giving the absorption bands at 1750, 1710, 1640 and 1240 cm$^{-1}$ assigned to ester-type C=O, ketone-type C=O, C=C and C—O—C linkages, respectively.

EXAMPLE 7

Into a reaction vessel were taken 100 ml of n-propyl alcohol, 14 g of 2-furylmethyl carbinol and 20.5 g of sodium acetate and 17.75 g of chlorine was introduced into the above mixture over a period of 20 minutes, while the temperature of the reaction mixture was kept at 20° to 30° C. under agitation which was continued further for 30 minutes after the end of the introduction of chlorine to complete the reaction. The reaction product purified in the same manner as in Example 1 was identified to be 2-propoxy-3,4-dichloro-6-methyl tetrahydropyran-5-one. The yield of the reaction product was 68% of the theoretical.

EXAMPLE 8

Into a reaction vessel were taken 100 ml of methyl alcohol, 14 g of 2-furylmethyl carbinol and 13.25 g (0.125 mole) of sodium carbonate, and the mixture was agitated to disperse the sodium carbonate. To the resulting reaction mixture which was kept at a temperature of about −20° C. was introduced 17.75 g of chlorine and, thereafter the temperature of the reaction mixture was gradually increased to 40° C. by heat evolved in the exothermic reaction, where the agitation was continued further for 30 minutes, to give 2-methoxy-3,4-dichloro-6-methyl tetrahydropyran-5-one in a yield of about 65% of the theoretical.

EXAMPLE 9

Into a reaction vessel were taken 14 g (0.125 mole) of 2-furylmethyl carbinol and 75 ml of methyl alcohol and 17.75 g (0.25 mole) of chlorine was introduced into the reaction mixture over a period of 20 minutes while the mixture was kept at a temperature of −20° to −30° C. Then the temperature of the reaction mixture was gradually increased to about 20° to 30° C. whereupon the color by the chlorine disappeared. After removal of the solvent, the reaction product was analyzed to be identified as 2-methoxy-3,4-dichloro-6-methyl tetrahydropyran-5-one. The yield of the product was about 60% of the theoretical.

EXAMPLE 10

About 61 g of 2-methoxy-3,4-dichloro-6-methyl tetrahydropyran-5-one was suspended in 600 ml of a 20% aqueous sulfuric acid solution and heated for 1.5 hours under reflux, followed by cooling and neutralization with a 20% aqueous solution of sodium hydroxide to a pH value of 3, and the reaction mixture was then extracted with methylene chloride. The extract was subjected to distillation to remove the solvent leaving 27 g of a solid product, which was identified to be 2-methyl-3-hydroxy-4-pyrone (maltol) by elementary analysis, infrared absorption spectral analysis, mass spectrometric analysis and NMR absorption spectral analysis. The yield of maltol was about 75% of the theoretical.

What is claimed is:

1. A tetrahydropyran-5-one compound represented by the general formula

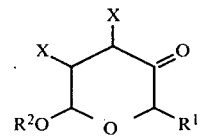

wherein R$^1$ is a hydrogen atom or a monovalent hydrocarbon group having 1 to 7 carbon atoms, R$^2$ is a monovalent hydrocarbon group having 1 to 7 carbon atoms or an acetyl group and X is a halogen atom.

2. A tetrahydropyran-5-one compound represented by the general formula

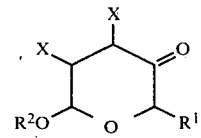

where R$^1$ is a hydrogen atom or a monovalent hydrocarbon group having 1 to 7 carbon atoms, R$^2$ is a methyl group, an ethyl group or an acetyl group, and X is a halogen atom.

3. The tetrahydropyran-5-one compound as claimed in claim 2 wherein R$^1$ is a methyl group.

4. The tetrahydropyran-5-one compound as claimed in claim 2 wherein R$^1$ is an ethyl group.

* * * * *